United States Patent
Chen

(10) Patent No.: US 11,793,334 B1
(45) Date of Patent: Oct. 24, 2023

(54) PROTECTIVE CASE OF CERVICAL TRACTION PILLOW AND CERVICAL TRACTION PILLOW

(71) Applicant: PLESON (HK) TECHNOLOGY LIMITED, Hong Kong (HK)

(72) Inventor: Xin Chen, Hong Kong (CN)

(*) Notice: Subject to any disclaimer, the term of this patent is extended or adjusted under 35 U.S.C. 154(b) by 0 days.

(21) Appl. No.: 18/082,196

(22) Filed: Dec. 15, 2022

(30) Foreign Application Priority Data

Nov. 25, 2022 (CN) .......................... 202223138279.9

(51) Int. Cl.
*A47G 9/10* (2006.01)

(52) U.S. Cl.
CPC ........ *A47G 9/1081* (2013.01); *A47G 2200/16* (2013.01)

(58) Field of Classification Search
CPC ...... A47G 9/10; A47G 9/1036; A47G 9/1072; A47G 9/1081; A47G 2200/16
See application file for complete search history.

(56) References Cited

U.S. PATENT DOCUMENTS

| | | | | |
|---|---|---|---|---|
| 4,858,259 A * | 8/1989 | Simmons | ................... | F25D 3/08 5/923 |
| 5,533,218 A * | 7/1996 | Fahy | ...................... | A47C 27/16 5/636 |
| 6,159,169 A * | 12/2000 | Lambden | .................. | A61F 7/08 601/39 |
| 10,201,240 B1 * | 2/2019 | Arrighi | ................. | A47G 9/1054 |
| 2007/0251013 A1 * | 11/2007 | Borror | ................. | A01K 1/0353 5/652 |
| 2011/0275966 A1 * | 11/2011 | Alkhattaf | ............. | A47G 9/1027 5/644 |
| 2014/0310877 A1 * | 10/2014 | Sternlight | ................ | A47G 9/02 5/639 |
| 2015/0150391 A1 * | 6/2015 | Hsu | ...................... | A47G 9/1081 5/636 |
| 2015/0257541 A1 * | 9/2015 | Lazakis | ................... | A61F 7/007 5/421 |
| 2015/0257554 A1 * | 9/2015 | Ross | ..................... | A47G 9/0215 5/639 |
| 2015/0297003 A1 * | 10/2015 | Ahroon | ..................... | G06T 7/33 206/38 |
| 2017/0071349 A1 * | 3/2017 | Wong | ..................... | A47C 7/383 |
| 2017/0246970 A1 * | 8/2017 | Maddocks | ............... | B60N 2/80 |
| 2018/0289183 A1 * | 10/2018 | Karl | ....................... | A47C 7/383 |
| 2019/0082867 A1 * | 3/2019 | Huang | ................. | A47G 9/1036 |
| 2020/0037798 A1 * | 2/2020 | Nardo | ...................... | A47G 9/10 |
| 2021/0030174 A1 * | 2/2021 | Romo | .................. | A47G 9/1081 |

* cited by examiner

*Primary Examiner* — David R Hare
*Assistant Examiner* — George Sun

(57) ABSTRACT

A protective case of a cervical traction pillow includes a traction pillow protective case main body and a heating device. The traction pillow protective case main body is used for covering a surface of a cervical traction pillow main body, and the heating device is arranged on the traction pillow protective case main body and/or the cervical traction pillow main body. By means of the above structure, so that when the traction pillow protective case main body covers the surface of the cervical traction pillow main body, the cervical traction pillow can be effectively prevented from getting dirty on the surface and breeding bacteria.

18 Claims, 4 Drawing Sheets

PROTECTIVE CASE OF CERVICAL TRACTION PILLOW AND CERVICAL TRACTION PILLOW

CROSS-REFERENCE TO RELATED APPLICATIONS

The application claims priority of Chinese patent application 2022231382799, filed on 2022 Nov. 25, which is incorporated herein by reference in its entireties.

TECHNICAL FIELD

The present disclosure relates to the field of traction pillows, in particular, to a protective case of a cervical traction pillow and a cervical traction pillow.

BACKGROUND

Cervical traction is a main measure to relieve the symptoms of cervical spondylosis because effective traction can relieve the compression of nerves blood vessels and spinal cord, and quickly relieve the symptoms of the cervical spondylosis. At present, pillows with a cervical traction function on the market can be used for cervical traction when a user takes a rest, but there are the following problems: First, since a user often uses a cervical traction pillow for cervical traction, the cervical traction pillow easily gets dirty and breeds bacteria after being used for multiple times, and are hard to clean. Second, the current cervical traction pillow can only simply drive the neck to do traction exercises, but cannot accelerate the blood circulation of the cervical vertebra resulting in a poor effect of cervical traction. Therefore, there is an urgent need to provide a protective case of a cervical traction pillow and a cervical traction pillow, which can prevent the cervical traction pillow from getting dirty, accelerate the blood circulation of the cervical vertebra while the cervical traction pillow drives the cervical vertebra to do traction exercises, improve the cervical traction effect, and relieve the fatigue of the cervical vertebra.

SUMMARY

In order to overcome the shortcomings of the prior art, the present disclosure provides a protective case of a cervical traction pillow and a cervical traction pillow, which can prevent the cervical traction pillow from getting dirty, accelerate the blood circulation of the cervical vertebra while the cervical traction pillow drives the cervical vertebra to do traction exercises, improve the cervical traction effect, and relieve the fatigue of the cervical vertebra.

The technical solution adopted by the present disclosure to solve the technical problem is as follows:

The present disclosure provides a protective case of a cervical traction pillow, including a traction pillow protective case main body and a heating device, wherein the traction pillow protective case main body is used for covering a surface of a cervical traction pillow main body, and the heating device is arranged on the traction pillow protective case main body and/or the cervical traction pillow main body.

As the improvement of the present disclosure, the traction pillow protective case main body is provided with an inner layer and an outer layer; an accommodating cavity is formed between the inner layer and the outer layer; and the heating device is arranged in the accommodating cavity.

As the improvement of the present disclosure, further including a temperature control device, wherein the temperature control device is electrically connected with the heating device; the temperature control device is used for controlling a surface temperature of the heating device; the temperature control device is a temperature control switch; and the temperature control switch is used for controlling a current flowing through the heating device to control the surface temperature the heating device.

As the improvement of the present disclosure, the traction, pillow protective case main body is also provided with a neck brace protective portion; the neck brace protective portion is used for covering a neck brace traction portion of the cervical traction pillow main body; and the heating device is arranged on a lower side of the neck brace protective portion and extends to an upper side of the neck brace protective portion.

As the improvement of the present disclosure, the traction pillow protective case main body is also provided with a power input port; the power input port is electrically connected with the heating device to supply power to the heating device; the protective case further includes a power supply module; and the power supply module is electrically connected with the heating device to supply power to the heating device.

As the improvement of the present disclosure, further including a wireless communication module, wherein the wireless communication module is electrically connected with the temperature control device to receive a wireless temperature control signal and control the surface temperature of the heating device.

As the improvement of the present disclosure, the heating device is a graphene heating sheet or a carbon fiber heating sheet or a composite fiber heating piece.

A cervical traction pillow also includes a cervical traction pillow main body and a protective case of a cervical traction pillow, the protective case of the cervical traction pillow including a traction pillow protective case main body and a heating device, wherein the traction pillow protective case main body is used for covering the surface of a cervical traction pillow main body, and the heating device is arranged on the traction pillow protective case main body and/or the cervical traction pillow main body.

As the improvement of the present disclosure, the cervical traction pillow main body is a flexible cervical traction pillow with a narrower upper part and a wider lower part, so as to form a neck brace traction portion at the upper end and a base at the lower end; an adjustment space is reserved between the neck brace traction portion and the base; the adjustment space is used for adjusting an angle and distance between the neck brace traction portion and the base to adjust a height and supporting angle of the cervical traction pillow main body.

As the improvement of the present disclosure, the neck brace traction portion, is provided with several massage convex points; a power supply accommodating slot is arranged in the base; and the power supply module is arranged in the power supply accommodating slot.

As the improvement of the present disclosure, the traction pillow protective case main body is provided with an inner layer and an outer layer, an accommodating cavity is formed between the inner layer and the outer layer; and the heating device is arranged in the accommodating cavity.

As the improvement of the present disclosure, further including a temperature control device, wherein the temperature control device is electrically connected with the heating device; the temperature control device is used for controlling a surface temperature of the heating device; the temperature control device is a temperature control switch; and the temperature control switch is used for controlling a current flowing through the heating device to control the surface temperature the heating device.

As the improvement of the present disclosure, the traction pillow protective case main body is also provided with a neck brace protective portion; the neck brace protective portion is used for covering a neck brace traction portion of the cervical traction pillow main body; and the heating device is arranged on a lower side of the neck brace protective portion and extends to an upper side of the neck brace protective portion.

As the improvement of the present disclosure, the traction pillow protective case main body is also provided with a power input port; the power input port is electrically connected with the heating device to supply power to the heating device; the protective case further includes a power supply module; and the power supply module is electrically connected with the heating device to supply power to the heating device.

As the improvement of the present disclosure, further including a wireless communication module, wherein the wireless communication module is electrically connected with the temperature control device to receive a wireless temperature control signal and control the surface temperature of the heating device.

As the improvement of the present disclosure, the heating device is a graphene heating sheet or a carbon fiber heating sheet or a composite fiber heating piece.

The beneficial effects of the present disclosure lie in: the present disclosure provides a protective case of a cervical traction pillow, the protective case of a cervical traction pillow includes the traction pillow protective case main body and the heating device; the traction pillow protective case main body is used for covering the surface of a cervical traction pillow main body, and the heating device is arranged on the traction pillow protective case main body and/or the cervical traction pillow main body, so that when the traction pillow protective case main body covers the surface of the cervical traction pillow main body, the cervical traction pillow can be effectively prevented from getting dirty on the surface and breeding bacteria. Furthermore, the heating device is arranged on the traction pillow protective case main body and/or the cervical traction pillow main body, so that when a user uses the cervical traction pillow for cervical traction, the heating device can generate heat and transfers the heat to the cervical vertebra of the user through the traction pillow protective case main body and/or the cervical traction pillow main body, so as to accelerate the blood circulation of the cervical vertebra of the user, improve the cervical traction effect and relieve the fatigue of the cervical vertebra.

BRIEF DESCRIPTION OF THE DRAWINGS

In order to explain the technical solutions of the embodiments of the present disclosure more clearly, the following will briefly introduce the accompanying drawings used in the embodiments. Apparently, the drawings in the following description are only some embodiments of the present disclosure. Those of ordinary skill in the art can obtain other drawings based on these drawings without creative work.

The present disclosure is further described below in detail in combination with the accompanying drawings and, embodiments.

DETAILED DESCRIPTION OF THE EMBODIMENTS

Embodiment I

Figure 1:
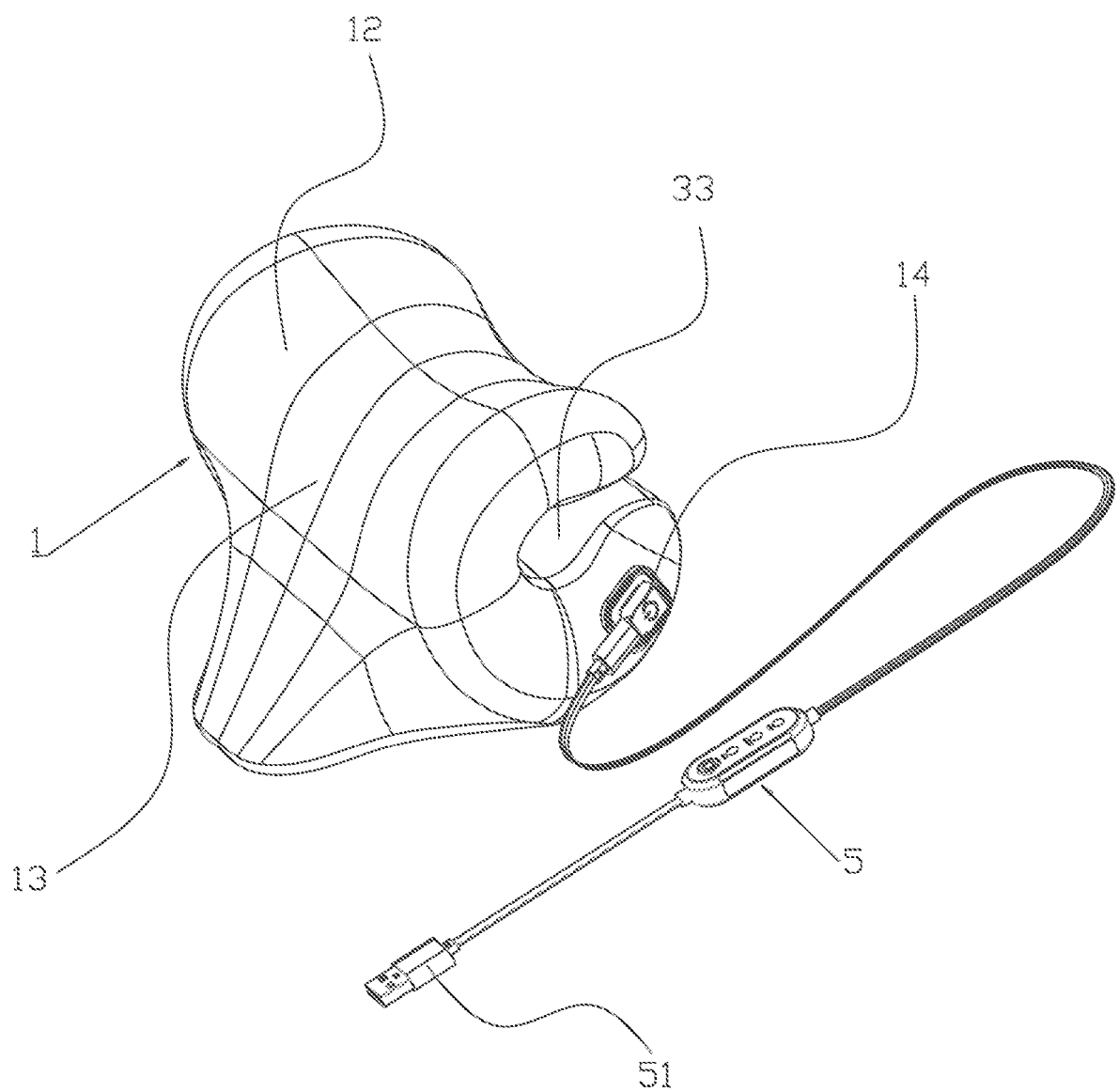
FIG. 1 is a schematic, diagram of an overall structure of the present disclosure.
Figure 2:
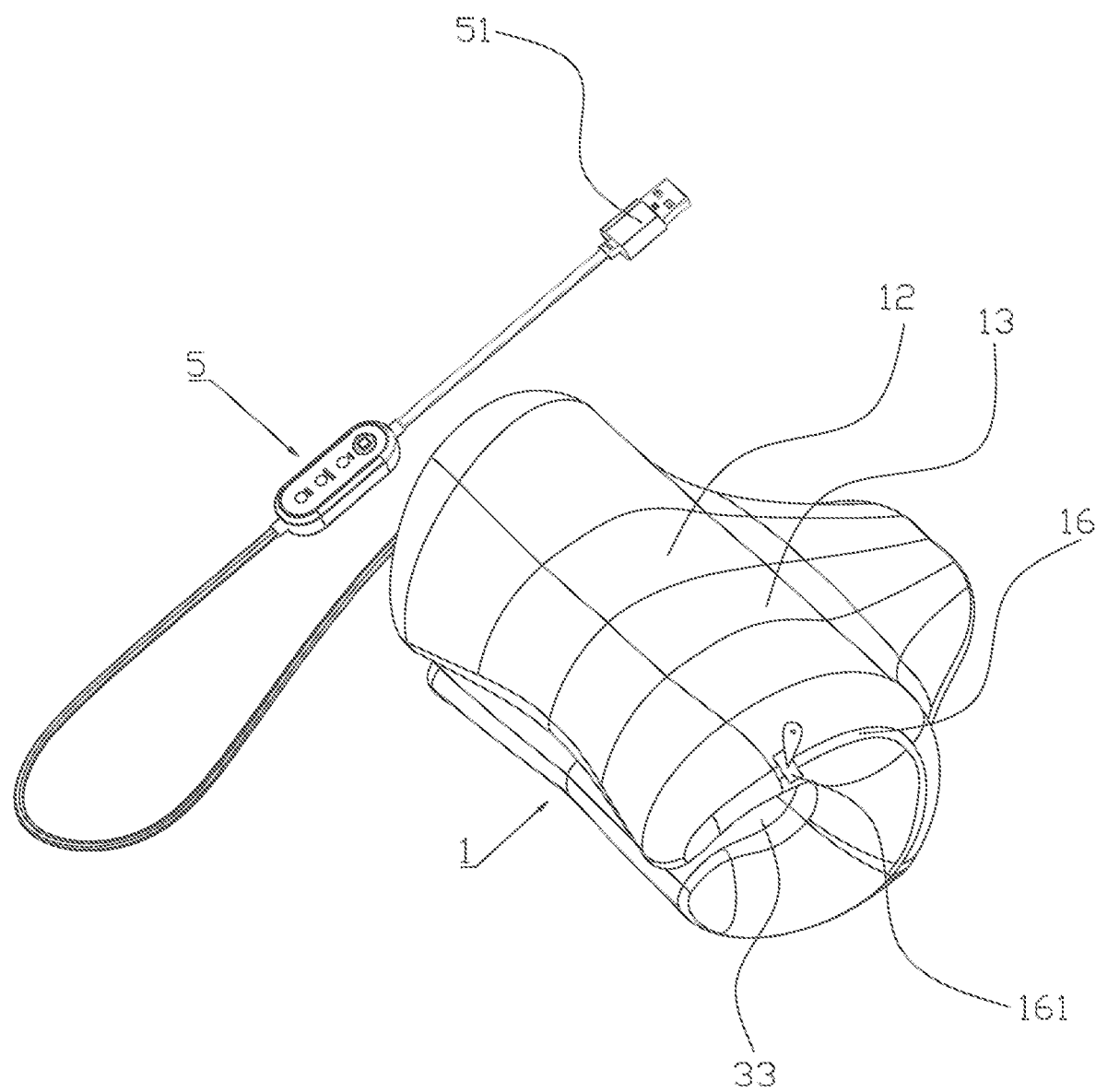
FIG. 2 is a schematic diagram of another overall structure of the present disclosure.
Figure 3:
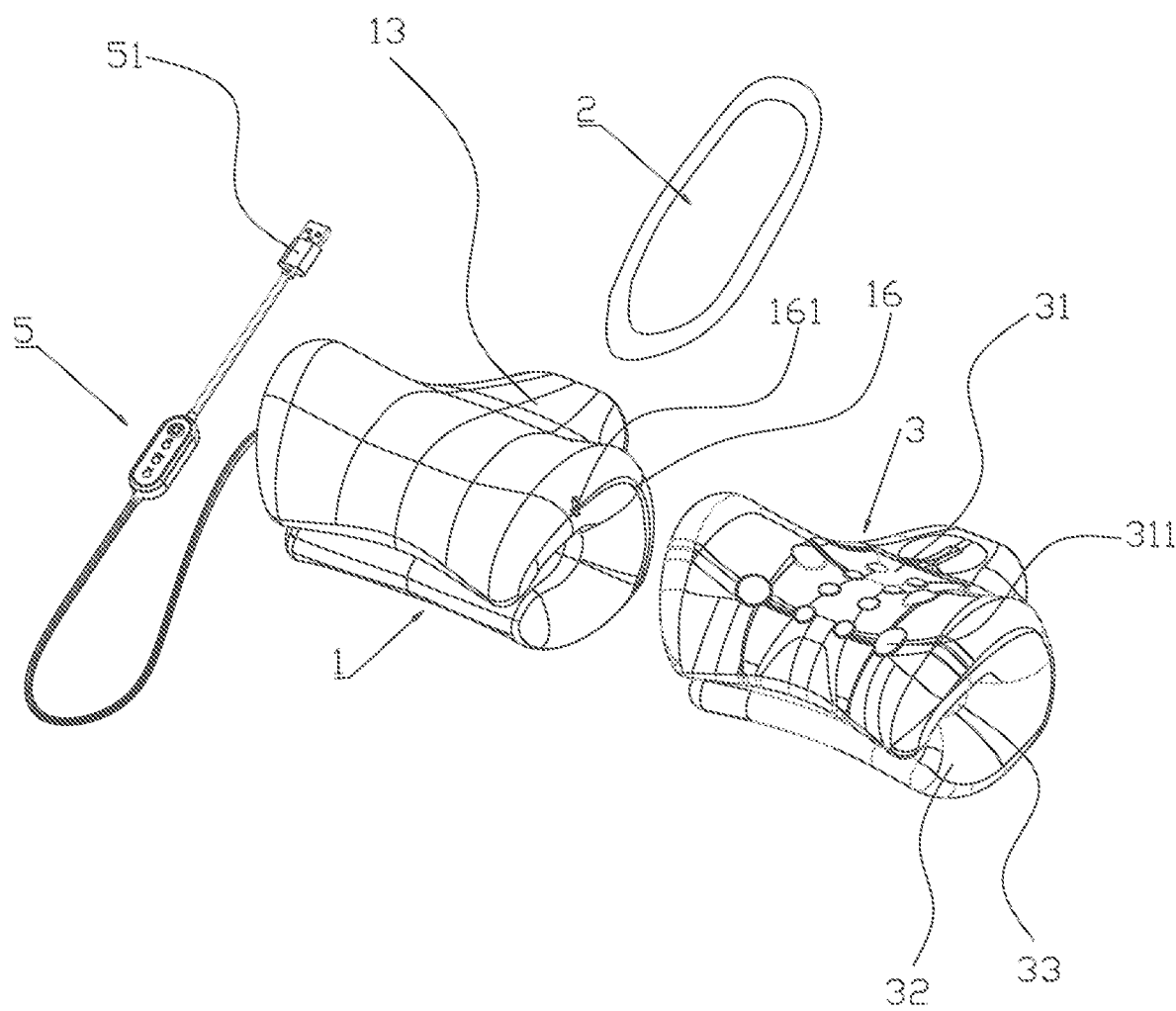
FIG. 3 is an exploded diagram of the present disclosure.
Figure 4:
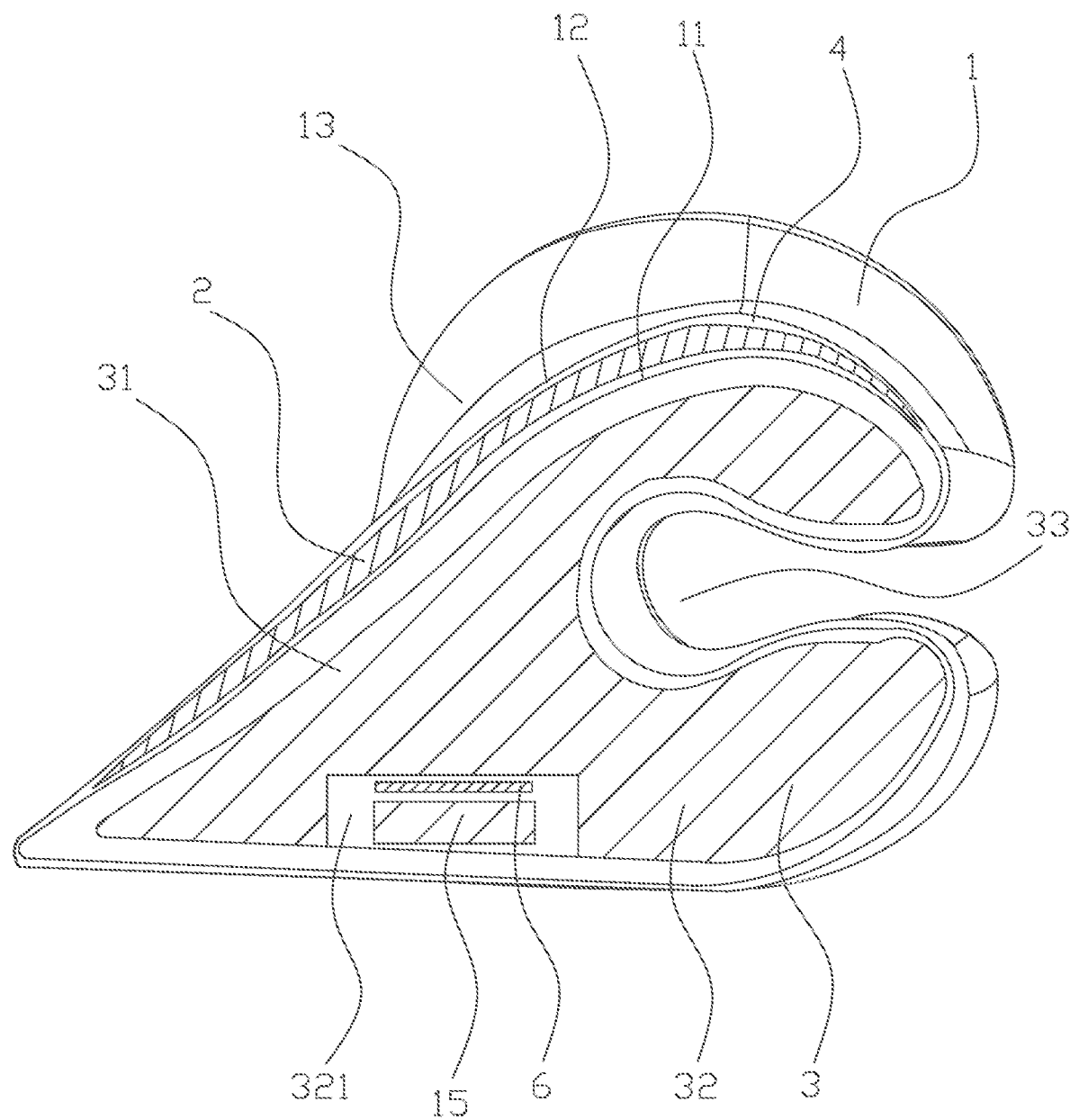
FIG. 4 is a sectional view sectioned along a heating device.

Referring to FIG. 1 to FIG. 4, a protective case of a cervical traction pillow includes a traction pillow protective case main body 1 and a heating device 2. The traction pillow protective case main body 1 is used for covering a surface of a cervical traction pillow main body 3, and the heating device is arranged on the traction pillow protective case main body 1 and/or the cervical traction, pillow main body 3. By means of the above structure, the protective case of a cervical traction pillow includes the traction pillow protective case main body and the heating device; the traction pillow protective case main body is used for covering the surface of a cervical traction pillow main body, and the heating device is arranged on the traction pillow protective case main body and/or the cervical traction pillow main body, so that when the traction pillow protective case main body covers the surface of the cervical traction pillow main body, the cervical traction pillow can be effectively prevented from getting dirty on the surface and breeding bacteria. Furthermore, the heating device is arranged on the traction pillow protective case main body and/or the cervical traction pillow main body, so that when a user uses the cervical traction pillow for cervical traction, the heating device can generate heat and transfers the heat to the cervical vertebra of the user through the traction pillow protective case main body and/or the cervical traction pillow main body, so as to accelerate the blood circulation of the cervical vertebra of the user, improve the cervical traction effect and relieve the fatigue of the cervical vertebra.

In this embodiment, the traction pillow protective case main body 1 is provided with an inner layer 11 and an outer layer 12. An accommodating cavity 4 is formed between the inner layer 11 and the outer layer 12. The heating device 2 is arranged in the accommodating cavity 4. By means of the above structure, the traction pillow protective case main body is provided with the inner layer and the outer layer; the accommodating cavity is formed between the inner layer and the outer layer; and the heating device is arranged in the accommodating cavity, which effectively achieves installation of the heating device, so that when the traction pillow protective case main body covers the surface of the cervical traction pillow main body, the cervical traction pillow can be effectively prevented from getting dirty on the surface sand breeding bacteria. Furthermore, the heating device is arranged in the accommodating cavity, so that when a user uses the cervical traction pillow for cervical traction, the heating device can generate heat and transfers the heat to the cervical vertebra of the user through the outer layer, so as to accelerate the blood circulation of the cervical vertebra of the user, improve the cervical traction effect and relieve the fatigue of the cervical vertebra.

In this embodiment, the protective case is further provided with a temperature control device 5. The temperature control device 5 is electrically connected with the heating device 2. The temperature control device 5 is used for controlling a surface temperature of the heating device 2. The temperature control device 5 is a temperature control switch. The temperature control switch is used for controlling a current flowing through the heating device 2 to control the surface temperature of the heating device 2. Specifically, the protective case further includes a wireless communication module 6. The wireless communication module 6 is electrically connected with the temperature control device 5 to receive, a wireless temperature control signal and control the surface temperature of the heating device 2. By means of the above structure, the user can control the surface temperature of the heating device through the temperature control switch. In addition, by the arrangement of the wireless communication module, the user can send a wireless temperature control signal to the temperature control switch by means of a remote controller, a mobile phone or other mobile terminals, so that the temperature control switch receives the wireless temperature control signal and controls the surface temperature of the heating device to realize a remote wireless temperature adjustment function.

In this embodiment, the traction pillow protective case main body 1 is also provided with a neck brace protective portion 13. The neck brace protective portion 13 is used for covering a neck brace traction portion 31 of the cervical traction pillow main body 3. The heating device 2 is arranged on a lower side of the neck brace protective portion 13 and extends to an upper side of the neck brace protective portion 13. The heating device 2 is a graphene heating sheet or a carbon fiber heating sheet or a composite fiber heating piece. By means of the above structure, the heating device is arranged on the lower side of the neck brace protective portion and extends to the upper side of the neck brace protective portion, so that the heat generated by the heating device can be radiated to the entire neck brace protective portion and the neck brace traction portion, so as to radiate the heat to the entire cervical vertebra of the user to accelerate the blood circulation of the cervical vertebra of the user, improve the cervical traction effect and relieve the fatigue of the cervical vertebra. Furthermore, the heating device is the graphene heating sheet or the carbon fiber heating sheet or the composite fiber heating piece, so that compared with a metal heating wire on the market, the graphene heating sheet, the carbon fiber heating sheet and the composite fiber heating piece generates heat immediately after being powered on, without preheating, have high heating efficiency and uniform heat, and can quickly generate heat and transfer it to the cervical vertebra of the user through the neck brace protective portion and the neck brace traction portion. The composite fiber heating wire is a metal fiber heating wire mainly prepared from iron, steel, nickel and the like. A metal is made to be wirelike by a special process and is then stranded into a rope. The carbon fiber heating wire which is mainly prepared from carbon accounting for 99% is nonmetal, belonging to a semiconductor. An electric heating principle of the carbon fiber heating wire is mainly generating heat energy by mutual collision of electric ions generated after the carbon fiber heating wire is powered on.

In this embodiment, the traction pillow protective case main body 1 is also provided with a power input port 14. The power input port 14 is electrically connected with the heating device 2 to supply power to the heating device 2. The protective case further includes a power supply module 15. The power supply module 15 is electrically connected with the heating device 2 to supply power to the heating device 2. The power input port is a TYPE C power input port, or a USB power input port, or other types of power input ports. Specifically, one end of the temperature control switch is electrically connected with the heating device through the power input port, and the other end of the temperature control switch is provided with a USB power outlet 51. The USB power outlet is connected to the outside. By means of the above structure, the power input port can supply power to the heating device, and the power supply module can be also charged by means of the power input port, so that the heating device of the protective case of a cervical traction pillow can be powered by mains supply or the power supply module. When the main supply is cut off or the user needs to go out with the cervical traction pillow covered with the protective case of a cervical traction, pillow, the heating device is powered by the power supply module, so that the user can enjoy the heating function of the heating device during cervical traction, so as to accelerate the blood circulation of the cervical vertebra of the user, improve the cervical traction effect and relieve the fatigue of the cervical vertebra. The power supply module can be a lithium battery or other types of batteries.

Embodiment II

A cervical traction pillow includes the above-mentioned protective case of a cervical traction pillow. By means of the above structure, the cervical traction pillow includes the traction pillow protective case main body and the heating device; the traction pillow protective case main body is used for covering the surface of a cervical traction pillow main body, and the heating device is arranged on the traction pillow protective case main body and/or the cervical traction pillow main body, so that when the traction pillow protective case main body covers the surface of the cervical traction pillow main body, the cervical traction pillow can be effectively prevented from getting dirty on the surface and breeding bacteria. Furthermore, the heating device is arranged on the traction pillow protective case main body and/or the cervical traction pillow main body, so that when a user uses the cervical traction pillow for cervical traction, the heating device can generate heat and transfers the heat to the cervical vertebra of the user through the traction pillow protective case main body and/or the cervical traction pillow main body, so as to accelerate the blood circulation of the cervical vertebra of the user, improve the cervical traction effect and relieve the fatigue of the cervical vertebra.

In this embodiment, the cervical traction pillow main body 3 is a flexible cervical traction pillow with a narrower upper part and a wider lower part, so as to form a neck brace traction portion 31 at the upper end and a base 32 at the lower end. An adjustment space 33 is reserved between the neck brace traction portion 31 and the base 32. The adjustment space 33 is used for adjusting an angle and distance between the neck brace traction portion 31 and the base 32 to adjust a height and supporting angle of the cervical traction pillow main body 3. By means of the above structure, the user can adjust the angle and distance between the neck brace traction portion and the base to adjust the height and supporting angle of the cervical traction pillow main body, so that the user can enjoy cervical traction under, a suitable supporting angle.

In this embodiment, the neck brace traction portion 31 is provided with several massage convex points 311. A power supply accommodating slot 321 is arranged in the base 32. The power supply module 15 is arranged in the power supply accommodating slot 321. By means of the above structure, the cervical traction pillow has a reasonable design and simple and compact structure, and effectively achieves the installation of the power supply module, and the cervical traction pillow with the protective case of a cervical traction pillow is still small and portable. In addition, when the main supply is cut off or the user needs to go out with the cervical traction pillow covered with the protective case of a cervical traction pillow, the heating device is powered by the power supply module, so that the user can enjoy the heating function of the heating device during cervical traction, so as to accelerate the blood circulation of the cervical vertebra of the user, improve the cervical traction effect and relieve the fatigue of the cervical vertebra.

In this embodiment, the traction pillow protective case main body 1 sleeves the surface of the cervical traction pillow main body 3 through a sleeving opening 16. The sleeving opening 16 is provided with a zipper 161 that is used for opening or closing the sleeving opening. By means of the above structure, the user can open the sleeving opening with the zipper, and conveniently sleeve and cover the surface of the cervical traction pillow with the traction pillow protective case main body. After the sleeving is completed, the sleeving opening can be closed with the zipper to prevent the traction pillow protective case main body from being separated from the surface of the cervical traction pillow. The cervical traction pillow has a simple structure and stable connection, so that it is convenient for the user to mount, replace and clean the traction pillow protective case main body. Further, the heating device is arranged on the traction pillow protective case main body, so that when the cervical traction pillow main body is damaged or aged and needs to be replaced, the sleeving opening can be opened with the zipper, and the user removes the traction pillow protective case main body provided with the heating device from the surface of the cervical traction pillow, and sleeves a new traction pillow main body with the traction pillow protective case main body 1 provided with the heating device, thus achieving repeated use of the traction pillow protective case main body and the heating device, which reduces the use cost of the user and is more environmentally friendly.

As described above, one or more embodiments are provided in conjunction with the detailed description, The specific implementation of the present disclosure is not confirmed to be limited to that the description is similar to or similar to the method, the structure and the like of the present disclosure, or a plurality of technical deductions or substitutions are made on the premise of the conception of the present disclosure to be regarded as the protection of the present disclosure.

What is claimed is:

1. A protective case of a cervical traction pillow, comprising a traction pillow protective case main body and a heating device, wherein the traction pillow protective case main body is used for covering a surface of a cervical traction pillow main body, and the heating device is arranged on the traction pillow protective case main body,
the traction pillow protective case main body comprises a pillow chamber configured for entirely accommodating the cervical traction pillow main body inside,
the traction pillow protective case main body comprises a bottom portion, a neck brace protective portion connected the bottom portion, a back portion connected between the neck brace protective portion and the bottom portion, and two side portions facing each other and connected the neck brace protective portion, the bottom portion and the back portion,
the neck brace protective portion is connected the bottom portion with an acute angle when the traction pillow protective case main body accommodating the cervical traction pillow main body inside,
the neck brace protective portion comprises an inner layer and an outer layer, an accommodating cavity is formed between the inner layer and the outer layer, the heating device is arranged in the accommodating cavity and extends from an end of the neck brace protective portion adjacent to the bottom portion to the other end of the neck brace protective portion adjacent to the back portion.

2. The protective case of the cervical traction pillow according to claim 1, further comprising a temperature control device, wherein the temperature control device is electrically connected with the heating device; the temperature control device is used for controlling a surface temperature of the heating device; the temperature control device is a temperature control switch; and the temperature control switch is used for controlling a current flowing through the heating device to control the surface temperature, of the heating device.

3. The protective case of the cervical traction pillow according to claim 1, wherein the traction pillow protective case main body is also provided with a power input port; the power input port is electrically connected with the heating device to supply power to the heating device; the protective case further comprises a power supply module; and the power supply module is electrically connected with the heating device to supply power to the heating device.

4. The protective case of the cervical traction pillow according to claim 2, further comprising a wireless communication module, wherein the wireless communication module is electrically connected with the temperature control device to receive a wireless temperature control signal and control the surface temperature of the heating device.

5. The protective case of the cervical traction pillow according to claim 1, wherein the heating device is a graphene heating sheet or a carbon fiber heating sheet or a composite fiber heating piece.

6. The protective case of the cervical traction pillow according to claim 1, wherein the back portion is configured to forming a "C" shaped structure when the traction pillow protective case main body accommodating the cervical traction pillow main body inside.

7. The protective case of the cervical traction pillow according to claim 1, wherein the traction pillow protective case main body further comprises a power input port, the power input port is electrically connected with the heating device to supply power to the heating device, and the power input port is disposed on one of the two side portions.

8. The protective case of the cervical traction pillow according to claim 1, wherein the traction pillow protective case main body sleeves the surface of the cervical traction pillow main body through a sleeving opening located at one of the two side portions, the sleeving opening is provided with a zipper that is used for opening or closing the sleeving opening.

9. A cervical traction pillow, comprising a cervical traction pillow main body and a protective case of a cervical traction pillow, the protective case of the cervical traction pillow comprising a traction pillow protective case main body and a heating device, wherein the traction pillow protective case main body is used for covering a surface of a cervical traction pillow main body, and the heating device is arranged on the traction pillow protective case main body,
the traction pillow protective: case main body comprises a pillow chamber configured for entirely accommodating the cervical traction pillow main body inside, the traction pillow protective case main body comprises a bottom portion, a neck brace protective portion connected the bottom portion, a back portion connected between the neck brace protective portion and the bottom portion, and two side portions facing each other and connected the neck brace protective portion, the bottom portion and the back portion, the neck brace protective portion is connected the bottom portion with an acute angle when the traction pillow protective case main body accommodating the cervical traction pillow main body inside, the neck brace protective portion comprises an inner layer and an outer layer, an accommodating cavity is formed between the inner layer and the outer layer, the heating device is arranged in the accommodating cavity and extends from an end of the neck brace protective portion adjacent to the bottom portion to the other end of the neck brace protective portion adjacent to the back portion.

10. The cervical traction pillow according to claim 9, wherein the cervical traction pillow main body is a flexible cervical traction pillow with a narrower upper part and a wider lower part, so as to form a neck brace traction portion at the upper end and a base at the lower end; an adjustment space is reserved between the neck brace traction portion and the base; the adjustment space is used for adjusting an angle and distance between the neck brace traction portion and the base to adjust a height and supporting angle of the cervical traction pillow main body.

11. The cervical traction pillow according to claim 10, wherein the neck brace traction portion is provided with several massage convex points; a power supply accommodating slot is arranged in the base; and the power supply module is arranged in the power supply accommodating slot.

12. The cervical traction pillow according to claim 9, further comprising a temperature control device, wherein the temperature control device is electrically connected with the heating device; the temperature control device is used for controlling a surface temperature of the heating device; the temperature control device is a temperature control switch; and the temperature control switch is used for controlling a current flowing through the heating device to control the surface temperature of the heating device.

13. The cervical traction pillow according to claim 12, further comprising a wireless communication module, wherein the wireless communication module is electrically connected with the temperature control device to receive a wireless temperature control signal and control the surface temperature of the heating device.

14. The cervical traction pillow according to claim 9, wherein the traction pillow protective case main body is also provided with a power put port; the power input port is electrically connected with the heating device to supply power to the heating device; the protective case further comprises a power supply module; and the power supply module s electrically connected with the heating device to supply power the heating device.

15. The cervical traction pillow according to claim 9, wherein the heating device is a grapheme heating sheet or a carbon fiber heating sheet or a composite fiber heating piece.

16. The cervical traction pillow according to claim 9, wherein the back portion is configured to forming a "C" shaped structure when the traction pillow protective case main body accommodating the cervical traction pillow main body inside.

17. The cervical traction pillow according to claim 9, wherein the traction pillow protective case main body further comprises a power input port, the power input port is electrically connected with the heating device to supply power to the heating device, and the power input port is disposed on one of the two side portions.

18. The cervical traction pillow according to claim 9, wherein the traction pillow protective case main body sleeves the surface of the cervical traction pillow main body through a sleeving opening located at one of the two side portions, the sleeving opening is provided with a zipper that is used for opening or closing the sleeving opening.

* * * * *